US009433646B2

(12) United States Patent
Ichim

(10) Patent No.: US 9,433,646 B2
(45) Date of Patent: Sep. 6, 2016

(54) METHODS OF INHIBITING GROWTH OF A NEOPLASTIC CELL

(71) Applicant: XON Cells, Inc., Germantown, MD (US)

(72) Inventor: Thomas E. Ichim, San Diego, CA (US)

(73) Assignee: XON CELLS, INC., Germantown, MD (US)

( * ) Notice: Subject to any disclaimer, the term of this patent is extended or adjusted under 35 U.S.C. 154(b) by 0 days.

(21) Appl. No.: 13/688,864

(22) Filed: Nov. 29, 2012

(65) Prior Publication Data
US 2013/0156847 A1 Jun. 20, 2013

Related U.S. Application Data

(63) Continuation of application No. 12/955,755, filed on Nov. 29, 2010, now abandoned, which is a continuation of application No. 11/486,635, filed on Jul. 13, 2006, now abandoned.

(60) Provisional application No. 60/699,579, filed on Jul. 14, 2005.

(51) Int. Cl.
*A61K 35/54* (2015.01)
*A61P 35/00* (2006.01)
*G01N 30/02* (2006.01)
*A61K 35/50* (2015.01)
*A61K 35/44* (2015.01)
*C12N 5/073* (2010.01)

(52) U.S. Cl.
CPC .............. *A61K 35/50* (2013.01); *A61K 35/44* (2013.01); *C12N 5/0605* (2013.01)

(58) Field of Classification Search
None
See application file for complete search history.

(56) References Cited

U.S. PATENT DOCUMENTS

| | | | |
|---|---|---|---|
| 4,054,648 A * | 10/1977 | Nagasawa et al. | 424/583 |
| 6,583,108 B1 * | 6/2003 | Tamburini et al. | 514/13.7 |
| 7,204,982 B2 | 4/2007 | Liau | |
| 2003/0211603 A1 | 11/2003 | Earp et al. | |
| 2004/0028660 A1 | 2/2004 | Hariri et al. | |
| 2004/0076618 A1 * | 4/2004 | Lee et al. | 424/93.7 |
| 2004/0185563 A1 | 9/2004 | De Santis | |
| 2006/0182724 A1 | 8/2006 | Riordan | |

OTHER PUBLICATIONS

Hingtgen et al, A First-Generation Multi-Functional Cytokine for Simultaneous Optical Tracking and Tumor Therapy, PLoS One, Jul. 2012, vol. 7 (7), pp. 1-10.*
Low et al, Inhibition of In Vitro Lymphocyte Proliferation by Ovine PLA, Journal of Reproductive Immunology, 1991 (19), pp. 25-41.*
Giannini et al, Histone deacetylase inhibitors in the treatment of cancer: overview and perspectves, Future Med Chem, 2012, 4(11), pp. 1439-1460.*
Bao et al, Potential use of drug carried-liposomes for cancer therapy via direct intratumoral injection, International Journal of Pharmaceutics 316 (2006) 162-169.*
Rostock et al, Anticancer Activity of a Lectin-rich Mistletoe Extract Injected Intratumorally into Human Pancreatic Cancer Xenografts, Anticancer Resarch, 2005, 25: 1969-1976.*
Manieri and Stappenbeck, Mesenchymal stem cell therapy of intestinal disease: are their effects systemic or localized? Curr Opin Gastroenterol. Mar. 2011 ; 27(2): 119-124.*
Fischer et al, Pulmonary Passage is a Major Obstacle for Intravenous Stem Cell Delivery: The Pulmonary First-Pass Effect, Stem Cells and Development, vol. 18, No. 5, 2009, p. 683-691.*
Angelucci et al. "The Growth of Malignant and Nonmalignant Human Cells is Modulated by a Human Placental Extract", *Anticancer Research*. 19(1A):429-436 (1999).
Cohen et al. "Umbilical cord blood transplantation—how, when and for whom?" *Blood Reviews*. 18(3):167-179 (2004).
Graham et al. (editors). *Subcellular Fractionation, A Practical Approach*. 1997. Oxford University Press.
Kim et al. "Histone Deacetylase in Carcinogenesis and Its Inhibitors as Anti-cancer Agents", *Journal of Biochemistry and Molecular Biology*. 36(1):110-119 (2003).
Klein et al. "Growth of only highly tumorigenic cell lines is inhibited by EAP, a human placental fraction", *Cancer Letters*. 70(1-2):91-99 (1993).
Klein et al. "Growth suppression of transformed cells by a human placental extract not related to transforming growth factor β", *Journal of Cancer Research and Clinical Oncology*. 117(3):192-196 (1991).
Liu et al. "Epigenetic Regulation of Human Telomerase Reverse Transcriptase Promoter Activity during Cellular Differentiation", *Genes, Chromosomes, and Cancer*. 41:26-37 (2004).
Lodygin et al. "Prostate cancer is characterized by epigenetic silencing of 14-3-3ó expression", *Oncogene*. 23:9034-9041 (2004).
McLaughlin et al. "Histone deacetylase inhibitors open new doors in cancer therapy", *Biochemical Pharmacology*. 68(6):1139-1144 (2004).
Mhawech et al. "Downregulation of 14-3-3ó in ovary, prostate and endometrial carcinomas is associated with CpG island methylation", *Modern Pathology*. 18:340-348 (2005).

(Continued)

*Primary Examiner* — Maria Marvich
(74) *Attorney, Agent, or Firm* — Knobbe, Martens, Olson & Bear LLP

(57) ABSTRACT

Disclosed are methods of preparing and using placentally-derived stem cells and compositions useful for the treatment of cancer. Said stem cells and compositions function through inducing a "guided differentiation" program in cancer cells, thereby reducing malignancy. Further extension of the invention pertains to augmenting ability of administered cells to induce differentiation through the co-administration of known differentiation inducing agents. Within the context of this disclosure, methods for inducing host responses to cancer are also described.

7 Claims, 10 Drawing Sheets

(56) References Cited

OTHER PUBLICATIONS

Zhong et al. "Induction of antitumor immunity through xenoplacental immunization", *Journal of Translational Medicine*. 4:1-9 (2006).

Zhong-Jing et al. "Effects of dendritic cells from cord blood CD34 cells on human hepatocarcinoma cell line BEL-7402 in vitro and in SCID mice", *World Journal of Gastroenterology*. 11(16):2502-2507 (2005).

Attar, E.C. and D.T. Scadden, Regulation of hematopoietic stem cell growth. Leukemia, 2004. 18(11): p. 1760-8.

Brittan, M. and N.A. Wright, Gastrointestinal stem cells. J Pathol, 2002. 197(4): p. 492-509.

Chaudhari, M., et al., Pancreatic stem cells: a therapeutic agent that may offer the best approach for curing type 1 diabetes. Pediatr Diabetes, 2001. 2(4): p. 195-202.

Craig, C.E., et al., The histopathology of regeneration in massive hepatic necrosis. Semin Liver Dis, 2004. 24(1): p. 49-64.

de Vries, E.G., et al., The happy destiny of frozen haematopoietic stem cells: from immature stem cells to mature applications. Eur J Cancer, 2004.40(13): p. 1987-92.

Ema, H. and H. Nakauchi, Self-renewal and lineage restriction of hematopoietic stem cells. Curr Opin Genet Dev, 2003.13(5): p. 508-12.

Hall, J.G., et al., Unrelated umbilical cord blood transplantation for an infant with beta-thalassemia major. J Pediatr Hematol Oncol, 2004. 26(6): p. 382-5.

Kaur, P., et al., Keratinocyte stem cell assays: an evolving science. J Investig Dermatol Symp Proc, 2004.9(3): p. 238-47.

Liu, L., et al., Epigenetic regulation of human telomerase reverse transcriptase promoter activity during cellular differentiation. Genes Chromosomes Cancer, 2004. 41(1): p. 26-37.

Lodygin, D., J. Diebold, and H. Hermeking, Prostate cancer is characterized by epigenetic silencing of 14-3-3sigma expression. Oncogene, 2004. 23(56):9034-9041.

Martino, G., How the brain repairs itself: new therapeutic strategies in inflammatory and degenerative CNS disorders. Lancet Neurol, 2004. 3(6): p. 372-8.

Mhawech, P., et al., Downregulation of 14-3-3sigma in ovary, prostate and endometrial carcinomas is associated with CpG island methylation. Mod Pathol, 2004. 18(3):340-348.

Michel, G., et al., Unrelated cord blood transplantation for childhood acute myeloid leukemia: a Eurocord Group analysis. Blood, 2003. 102(13): p. 4290-7.

Rocha, V., G. Sanz, and E. Gluckman, Umbilical cord blood transplantation. Curr Opin Hematol, 2004. 11(6): p. 375-385.

Rookmaaker, M.B., et al., Progenitor cells in the kidney: biology and therapeutic perspectives. Kidney Int, 2004. 66(2): p. 518-22.

\* cited by examiner

Figure 10

|  | Tumour Areas (mm) at Days Post Tumour Implant: | | | |
|---|---|---|---|---|
| Animal # : | Day 15 | Day 20 | Day 25 | Day 50 |
| 1 Control | 64.6 | 133.0 | Dead | - |
| 2 Control | 103 | 212 | 300 | Dead |
| 3 Control | 45 | 205 | 331 | Dead |
| 4 Control | 74 | 122 | 153 | Dead |
|  |  |  |  |  |
| 5 Treated | 122.9 | 34.4 | 36.1 | 8.3 |
| 6 Treated | 34.8 | 48.1 | 92.9 | No tumor |
| 7 Treated | 64.6 | 58.2 | 117.8 | 32 |
| 8 Treated | 30.4 | 47.5 | 0.96 | No tumor |
| 9 Treated | 33 | 54.5 | 40.2 | 14.3 |
| 10 Treated | 62 | 55.5 | 3.3 | No tumor |
| 11 Treated | 55 | 45.2 | 38.2 | 21.6 |

METHODS OF INHIBITING GROWTH OF A NEOPLASTIC CELL

CROSS-REFERENCE TO RELATED APPLICATIONS

This application is a continuation of U.S. application No. 12/955,755, filed on Nov. 29, 2010, now abandoned, which is a continuation of U.S. application No. 11/486,635, filed on Jul. 13, 2006, now abandoned, both of which were entitled METHODS OF INDUCING CELL DIFFERENTIATION WITH PLACENTAL EXTRACTS, which claimed priority under 35 U.S.C. §119 to U.S. Provisional Application No. 60/699,579, which was filed on Jul. 14, 2005, the disclosure of each of which is hereby incorporated by reference in its entirety.

BACKGROUND

1. Field of the Invention

The invention disclosed relates generally to the fields of cancer therapy. More particularly, it relates to the process of cancer cell differentiation into cells of reduced malignancy, or lacking of malignancy. More specifically, the invention pertains to the utilization of cord-blood and placentally derived stem cells for the stimulation of cancer cell differentiation.

2. Description of Related Art

In the field of cellular biology, the definition of "stem cell" is dependent on function more than on morphology. The characteristic function of a stem cell is the ability to both self-renew and to differentiate. Stem cells differentiate upon need of the host in response to a wide variety of stimuli, these include the need for increased erythrocytes due to high altitude, or the need for augmented numbers of neutrophils in response to a bacterial infection [1]. Additionally, stem cells can be artificially induced to replicate through various means including administration of cytokines, growth factors, and small peptides [2]. A wide variety of tissue-specific stem cells have been identified, these include liver [3], skin [4], renal [5], pancreatic [6], gastric [7] and neuronal [8].

There are many similarities between neoplastically transformed tissue and stem cells in the sense that both express embryonic-like features, including the ability to migrate (metastasize), ability to suppress immune responses, and ability to proliferate. The sole difference resides in the fact that stem cells are highly regulated in terms of growth and differentiation, whereas cancer cells are not. At the molecular level, the more aggressive a cancer is, the more de-differentiated and "stem cell-like" it becomes. Specifically, regions of DNA that are transcriptionally silenced in mature tissue, become active when the tissue turns cancerous. For example the enzyme telomerase is needed for cells to escape proliferative senescence (ie multiple past the Hayflick limit). Stem cells possess active telomerase, in similarity to cancer cells. In contrast, as cells differentiate into specialized tissue, telomerase expression becomes silenced epigenetically through synergistic involvement of DNA methylation and histone deacetylation [9]. Conversely, tumor cells selectively silence, again through epigenetic mechanisms, genes that stop the tumor from being neoplastic. For example it is known that in prostate cancer tumor suppressor genes become silenced by methylation [10]. In fact, this is a common phenomena seen in a wide variety of histologically-differing tumors [11].

Stem cells actively secrete differentiation inducing factors, both known and unknown, that are capable of inducing epigenetic reprogramming in cells. In U.S. Patent Publication No. 2003/0211603 (Earp et al., hereby incorporated by reference in its entirety) disclose that embryonic stem cells possess the ability to reprogram differentiated cells to take a "de-differentiated" phenotype. Although the subject matter did not indicate potential application to cancer cells, such an application would be counterintuitive since more dedifferentiated tumors would be expected to possess increased malignancy. The invention disclosed in this patent is based on the unique and unanticipated discovery that such "reprogramming" of cancer cells does not lead to increased malignancy but instead induces a differentiation program which results in formation of normal, or normal-like progenitors.

Cord blood is a rich source of hematopoietic stem cells, capable of reconstituting the hematopoietic lineage in NOD-SCID mice. The potential utilization of cord blood stem cells, such as CD34+ cells, has led to the cryopreservation of such cells for more than a decade [12]. Indeed, the clinical use of cord blood derived stem cells is becoming increasing acceptable as an alternative to bone marrow transplant, or cytokine mobilized peripheral blood stem cell transplant for a wide variety of diseases. This is in part because of a reduced incidence of graft versus host reaction using cord blood stem cells in comparison with other sources [13]. Indeed, this was observed in pediatric leukemia patients lacking suitable major histocompatibility complex (MHC) matched donors [14], as well as in transplantation of patients with certain anemias or hematopoietic stem cell disorders such as beta-thalassemia major [15].

Placental extracts have also been previously described in the art. For example, a low molecular weight fraction of placental tissue is known to be immunosuppressive as reported by Chauaot. Additionally, the use of placenta in cosmetics is well known. Therefore, placenta and cord-blood are two accepted sources of biomaterial that is innocuous for human use.

SUMMARY OF THE INVENTION

The invention described in the present disclosure teaches methods of generating compositions therapeutically useful for treatment of cancer patients. While chemotherapy and radiation therapy induce severe side effects through collateral damage to non-cancerous cells and organs, the present invention utilizes the ability of cancer cells to be "reprogrammed" into benign, non-cancerous progeny. The use of cellular differentiation therapy has been previous attempted in cancer patients; however, the majority of such differentiation inducers have been synthetic chemicals administered at unnaturally high doses.

In the present invention, the inventor teaches the utilization of stem cells to guide the differentiation of cancer cells into non-malignant cells. For example, it is disclosed that the administration of cord blood stem cells to a cancer patient is demonstrated to have some anticancer effect. This effect is magnified if certain derivatives from the cord blood stem cells are systemically administered. Said derivatives include the low molecular weight fraction that can be purified through column chromatography. Other methods of separation include high performance liquid chromatography, Fas Q liquid chromatography, or on-line mass spectrometry.

A simpler method of concentrating the differentiation inducing abilities of the cord blood stem cells is through purified the cell culture supernatant of said cells through solid phase adsorption such as through the use of a C-18 columns. The therapeutic composition can also be produced in a more convenient manner through utilization of placenta lysate concentrated by C-18.

Noted within the disclosure is that cancer cells treated with differentiation inducing agents possess an inhibited proliferative index. This is attributed to the fact that the differentiation inducing composition endows the neoplastic cells with a more benign phenotype (i.e. reduced proliferation).

The present disclosure is not intended to be limiting in any way and can be practiced with other techniques known to one skilled in the art. For example, co-administration of placental extract with differentiation inducers known in the art is within the scope of the invention.

Additionally, it is known that differentiated cells express antigens not found in immature progeny. U.S. Patent Publication No. 2004/0185563, hereby incorporated by reference in its entirety, describes a method of increasing efficacy of immunotherapy by induction of neoantigens on cancer cells through differentiation by administration of histone deacetylase inhibitors. An application of the invention disclosed includes the utilization of stem cell derivatives for increasing the immunogenicity of tumor tissue. This would result in sensitization to conventionally used immune stimulatory anticancer approaches including but not limited to cancer vaccines, cytokine therapy, and non specific immune stimulators such as BCG, CpG, or beta glucan.

In some embodiments, a composition comprising placentally-derived tissue extract and cells is provided, which is capable of inducing the differentiation of a substantially neoplastic cell into a cell with benign characteristics. The placental tissue can be human. The neoplastic cell can possess one or more of the following characteristics: invasiveness, ability to metastasize, ability to suppress immune response, ability to proliferate past the Hayflick limit. The neoplastic cell can be chosen from, for example, the group of cancers consisting of: a soft tissue sarcoma, a lymphoma, a cancer of the brain, an esophageal cancer, a uterine cancer, a cancer of the cervix, a bone cancer, a lung cancer, a cancer of the endometrium, a bladder cancer, a breast cancer, a cancer of the larynx, a cancer of the colon/rectum, a stomach cancer, a cancer of the ovary, a pancreatic cancers, an adrenal gland cancer and a prostate cancer. The cell with benign characteristics can be, for example, a cell that lacks one or more of the following: invasiveness, ability to metastasize, ability to suppress immune response, and ability to proliferate past the Hayflick limit. The placental tissue may be processed, for example, through collagenase or other cell dissociating methods, followed by purification of single cells. For example, the cellular purification can be performed using Percoll gradient of 0.3 mg/ml or other density gradients. The placentally-derived cells can be, for example, cord blood stem cells, mesenchymal stem cells, or other placentally derived stem cells. The placentally-derived cells and tissue extract can be administered, for example, to a patient in need thereof together with a compound capable of inducing cellular differentiation. The compound capable of inducing cellular differentiation can be, for example, dihydroxyvitamin D3, retinoic acid, valproic acid, or a histone deacetylase inhibitor. The histone deacetylase inhibitor can be, for example, trichostatin A, a short-chain fatty acid, a hydroxamate, a cyclic tetrapeptide, or a benzamide. The composition can be used as an adjuvant to a chemotherapeutic drug.

In additional embodiments, a method of reducing malignancy of a tumor in a patient is provided, by extracting placental tissue obtained from a healthy mother, homogenizing said tissue and obtaining a single cell suspension, purifying CD34+ cells, and administering the CD34+ cells to a patient in need thereof. The CD34+ cells can be, for example, co-administered with a differentiation-inducing agent. The CD34+ cells can be, for example, expanded in vitro prior to administration. The expansion can be performed by culture in media conditioned with cytokines and/or growth factors selected from the following: leukemia inhibitory factor, IL-1 through IL-13, IL-15 through IL-17, IL-19 through IL-22, granulocyte macrophage colony stimulating factor (GM-CSF), granulocyte colony stimulating factor (G-CSF), macrophage colony stimulating factor (M-CSF), erythropoietin (Epo), thrombopoietin (Tpo), Flt3-ligand, B cell activating factor, artemin, bone morphogenic protein factors, epidermal growth factor (EGF), glial derived neurotrophic factor, lymphotactin, macrophage inflammatory proteins, myostatin, neurturin, nerve growth factors, platelet derived growth factors, placental growth factor, pleiotrophin, stem cell factor, stem cell growth factors, transforming growth factors, tumor necrosis factors, Vascular Endothelial Cell Growth Factors, and fibroblast growth factors, FGF-acidic and basic fibroblast growth factor. In additional embodiments, one or more genes can be transfected into the CD34+ cells prior to administration. The transfected genes can be associated with inhibition of tumor growth. The transfected genes can be selected from the group consisting of: IFN-g, IL-2, IL12, IL-15, IL-18, IL-23.

A chemotherapeutic agent can also be co-administered with the CD34+ cells. The chemotherapeutic agent can be chosen from, for example, methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MM1270, BAY 12-9566, RAS farnesyl transferase inhibitor, farnesyl transferase inhibitor, MMP, MTA/LY231514, LY264618/Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, Incel/VX-710, VX-853, ZD0101, ISI641, ODN 698, TA 2516/Marmistat, BB2516/Marmistat, CDP 845, D2163, PD183805, DX8951f, Lemonal DP 2202, FK 317, Picibanil/OK-432, AD 32/Valrubicin, Metastron/strontium derivative, Temodal/Temozolomide, Evacet/liposomal doxorubicin, Yewtaxan/Placlitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT (Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, ZD1839, LU 79553/Bis-Naphtalimide, LU 103793/Dolastain, Caetyx/liposomal doxorubicin, Gemzar/Gemcitabine, ZD 0473/Anormed, YM 116, iodine seeds, CDK4 and CDK2 inhibitors, PARP inhibitors, D4809/Dexifosamide, Ifes/Mesnex/Ifosamide, Vumon/Teniposide, Paraplatin/Carboplatin, Plantinol/cisplatin, Vepeside/Etoposide, ZD 9331, Taxotere/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosfamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2' deoxycoformycin), Semustine (methyl-CCNU), Teniposide (VM-26) and Vindesine sulfate.

In an additional embodiment, a cell free extract capable of inducing differentiation in cancer cells is provided, which is produced by extracting human placenta; homogenizing said placenta, resulting in a homogenate; centrifuging said homogenate in order to free the supernatant of cellular debris; purifying differentiation associated molecular weight fractions; and administering said fractions to a patient in need thereof. The purified, differentiation-inducing fraction can have, for example, a molecular weight of 10-10,000 Daltons, or a molecular weight of 300-3,000 Daltons. The cell-free extract can be used in a method of stimulating an immune response to cancer cells by administration of the extract, together with an appropriate immunological adjuvant. In additional embodiments, a method of prophylactically treating a cancer patient is provided by administration of the cell free extract a patient in need thereof. In an additional embodiment, a method of inhibiting progression of a preneoplastic lesion to neoplasia is provided, by administration of the cell free extract. The cell free extract can, for example, be derived from bone marrow stem cells or unpurified bone marrow nucleated cells as an alternative to cord blood or other placentally-derived cells.

In an additional embodiment, a differentiation inducing composition, suitable for administration to a patient in need thereof, and derived from placental tissue is provided, by extracting human placenta, homogenizing the placenta, resulting in a homogenate, centrifuging the homogenate in order to free the supernatant of cellular debris, purifying the cell free-debris through adsorption on a C-18 column; and filter sterilizing the composition. The homogenized portion of the placenta may consist substantially of, for example, chorionic tissue. A histone deacetylase inhibitor can be added directly to the composition. In additional embodiments, a the composition can be administered intratumorally in a method of inducing differentiation and reprogramming of distal cancer lesions. In additional embodiments, a method of substantially increasing efficacy of the composition is provided, by administration in a liposomal complex. A substantially purified therapeutic composition can be prepared, for example, by preparing a supernatant, subjecting the supernatant to solid phase extraction to produce a product, subjecting the resulting product to gel filtration to produce a product, subjecting the resulting product to anion exchange fast phase liquid chromatography to produce a product, subjecting the resulting product to amino-high performance liquid chromatography to produce a product, and subjecting the resulting product to reverse phase high performance liquid chromatography to produce purified differentiation inducing factor. The supernatant can be prepared, for example, by culturing cord-blood derived stem cells to produce a factor-containing supernatant, or by centrifugation of lysed placental extract.

DESCRIPTION OF FIGURES

The foregoing aspects and many of the attendant advantages of this invention will become more readily appreciated as the same becomes better understood by reference to the following detailed description, when taken in conjunction with the accompanying drawings, wherein:

FIG. 10 is a table showing the inhibition of Lewis Lung Carcinoma growth using placental extract.

DETAILED DESCRIPTION OF THE INVENTION

Figure 1:
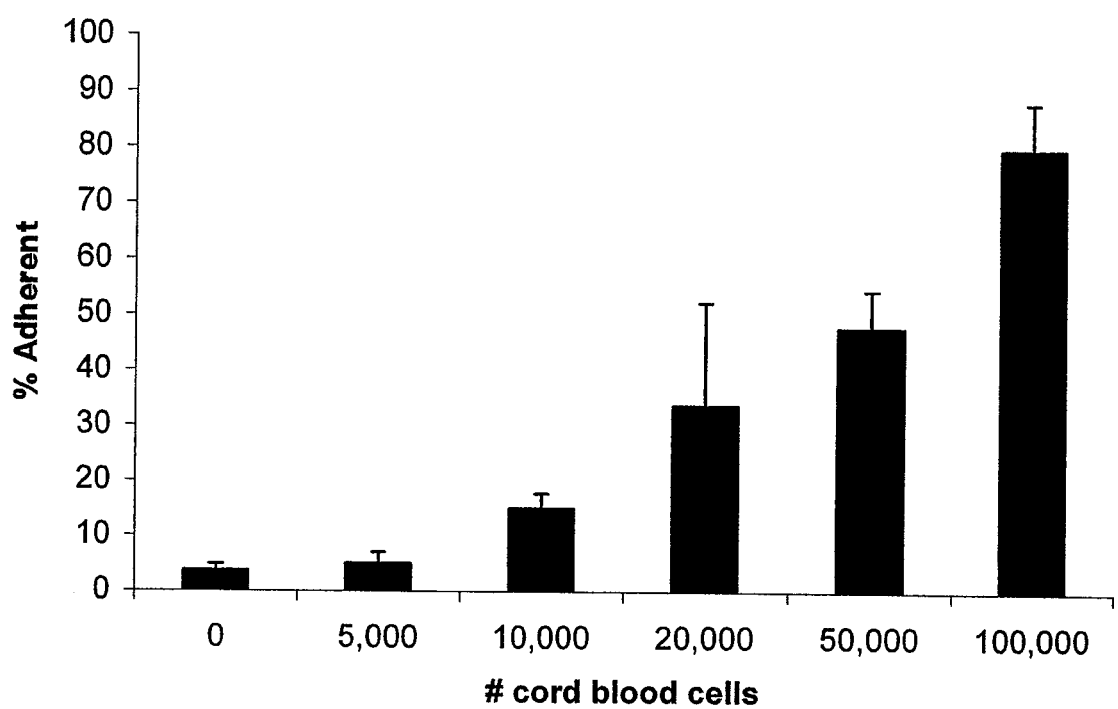
FIG. 1 is a bar graph demonstrating the induction of HL-60 differentiation in vitro by co-culture with cord blood nucleated cells.

Without intending to be limited by theory, it is also hypothesized that factors present in the culture of cord blood stem cells have the ability to induce a differentiation program in cancer cells in effect, to begin a reprogramming process that endows the cell an ability to make progeny with benign, noncancerous, or semicancerous phenotype. Simultaneously or subsequently, the cell encounters growth conditions or agents that promote differentiation down another differentiation pathway. These ideas are placed here for the interest of the skilled artisan, and do not need to be understood to put the invention into practice. The claimed invention is not restricted by mechanism of action, and is limited only by the features explicitly stated, as interpreted by one skilled in the art.

The invention described teaches methods of inducing the differentiation of cancer cells in a host in need thereof through administration of cells or factors derived from said cells that possess stem cell like properties. Specifically, the differentiation-inducing capabilities of the compositions described are useful for the treatment of breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, malignant melanomas, and epidermoid carcinomas.

As described herein, cells with stem cell activity, such as cord blood cells, can be derived from human placental tissue. Thus, the terms "placentally derived tissues" and "placentally derived cells" can include cord blood cells.

In some embodiments, cells with stem cell like activity are purified from human placenta using antibody mediated cell depletion followed by positive selection. Methods of depleting lineage positive cells are well known in the art and include the use of antibodies to the lineage antigens (CD5, CD45R (B220), CD11b, anti-Ly-6G (Gr-1), 7-4, and Ter-119) followed by complement depletion. A less damaging protocol involves utilization of magnetically bound antibodies and depletion by use of magnetic separation. This protocol is well known in the art and is commercially available using the Magnetic Activated Cell Sorting (MACS) technology offered by Miltenyi Biotech. Further purification of cells with stem cell activity can be performed by selection for the stem cell antigen CD34. Selection can be accomplished again by magnetic separation using the "positive selection" method, or alternatively by fluorescent activated cell sorting (FACS). Other methods of purifying cells with stem cell activity include use of Wheat Germ Agglutinin, or selection for low density profile using a chemical gradient such as Percoll.

Methods for expansion of stem cell populations have been described. For example, U.S. patent application Ser. No. 11/353,692 filed on Feb. 14, 2006, entitled METHOD FOR EXPANSION OF STEM CELLS, describes a method of increasing the growth of stem cells by mixing the stem cells with a growth medium that has been conditioned by an incubation with placental tissue. This method increases the expansion of the stem cell population. This patent application is incorporated by reference herein in its entirety.

Cells with stem cell activity are recognized by ability to reconstitute severe combined immunodeficiency mice with multilineage human blood populations as determined by the species specific marker CD45. Other methods of assessing the "stem cell" ability of purified cord blood cells includes plating said cells in methylcellulose in the presence of differentiation-inducing factors and assessing for production of multilineage colonies. For example, plating in the presence of G-CSF would induce formation of granulocytes, plating in the presence of EPO would induce erythrocyte formation, and plating in the presence of thrombopoietic would induce colonies consisting of megakaryocytes.

Upon purification of a stem cell population, the cells can be administered directly into a cancer patient through parenteral introduction, comprising intramuscular, intravenous, peritoneal, subcutaneous, intradermal, as well as topical administration. A preferred method of administration is intravenous, however, various compositions of the cells can be derived by one skilled in the art. For example, when treating a patient with melanoma, the purified cord blood stem cells can be lyzed and admixed with transdermal carrying agents for effective direct delivery. Transdermal carriers include systems such as iontophoretic and sonophoretic systems, thermosetting gels, and prodrugs. For enhanced uptake, absorption promoters may be utilized. The absorption promoters may be selected in particular, from propylene glycol, hexylene glycol, propylene glycol dipelargonate, glyceryl monoethyl ether, diethylene glycol, monoglycerides, monooleate of ethoxylated glycerides (with 8 to 10 ethylene oxide units), Azone (1-dodecylazacycloheptan-2-one), 2-(n-nonyl)-1,3-dioxolane, isopropylmyristate, octylmyristate, dodecyl-myristate, myristyl alcohol, lauryl alcohol, lauric acid, lauryl lactate, terpinol, 1-menthol, d-limonene, β-cyclodextrin and its derivatives or surfactants such as polysorbates, sorbitan esters, sucrose esters, fatty acids, bile salts, or alternatively lipophilic and/or hydrophilic and/or amphiphilic products such as poly-glycerol esters, N-methylpyrrolidone, polyglycosylated glycerides and cetyl lactate. The absorption promoter preferably represents from 5 to 25% of the weight of the composition. Further description of absorption promoters appears in U.S. Pat. No. 6,538,039, which is hereby incorporated by reference in its entirety.

In terms of administrating the cells through the intravenous route, several modifications can be made to the cells to increase efficacy, this includes transfection with suicide genes, immune stimulatory genes, or genes which encode pro-drug activating enzymes. Additionally, the cord blood stem cells may be labeled in order to detect presence of tumor cells.

Typical administration of cells is performed based on the therapeutic need of the patient. In a standard embodiment, cord blood stem cells are infused intravenously in a physiologically suitable solution such as albumin with saline. Cell concentrations may range from $10^3$-$10^9$ CD34+ cells/kg. Frequency may include weekly, daily, or depending on status of tumor growth as determined by biomarkers, imaging or patient general medical condition.

Another embodiment deals with using placental extracts as a heterogeneous starting point for preparation of a pharmaceutical agent. This embodiment uses full term, healthy, pathogen free chorions obtained from deliveries or cesarean sections deliveries. Many methods exist for preparation of cell lysate. Cell lysis procedures were extensively described in US Patent Publication No. 2003/0211603, hereby incorporated by reference in its entirety. Procedures described therein are modified for cord blood stem cells. For example, cell lysate or extract can be prepared from cord blood stem cell cultures or bone marrow stem cell cultures. Before lysing, the cells typically are allowed to recover after the last passage by culturing for about 2-3 days in standard medium until the culture is at least about 50% confluent. The cells can be lysed directly in the culture dish, for example, by replacing the medium with a solubilizing liquid, or by repeated freeze-thawing. Alternatively, the cells can be resuspended from the culture surface before lysis, for example, by brief collagenase digestion, or by scraping. The resuspended cells are collected, for example, by centrifugation, and then lysed by adding a suitable solvent, by freeze-thawing, by shearing through a narrow-gauge needle or in a tissue grinder, by sonicating, by mechanical homogenization, or by any other suitable method. In certain circumstances, subcellular organelles can be removed or enriched, or membrane fractions can be prepared, according to standard methods. Techniques in subfractionating cells to produce cell components and extracts can be found in Storrie et al., Meth. Enzymol. 182:203, 1990; and in Subcellular Fractionation: A Practical Approach (Grahan & Rickwood, eds., Oxford, 1997), both of which are hereby incorporated by reference in their entirety. Viscosity of the cell extract caused by long-chain nucleic acids can be reduced by treating with DNAse, or other appropriate nucleases. Non-ionic detergents with a high critical micelle concentration (such as sodium deoxycholate) can be removed by dialysis. Other detergents (such as Triton™ X-100, octyl glucoside, or Nonidet™-P40) can be removed, for example, on adsorbent beads or chromatography columns. Large particulates can be removed, for example, by centrifugation or microfiltration. As another option, high molecular weight solutes can be concentrated from the clarified extract (for example, by microfiltration, salt precipitation, column chromatography, or lyophilization).

In accordance with a further embodiment, a method is provided for preparing a purified cancer differentiation inducing factor comprising the steps of
  (a) culturing cord-blood derived stem cells to produce a factor-containing supernatant;
  (b) subjecting the supernatant to solid phase extraction to produce a product;
  (c) subjecting the product from step (b) to gel filtration to produce a product;
  (d) subjecting the product from step (c) to anion exchange fast phase liquid chromatography to produce a product;
  (e) subjecting the product from step (d) to amino-high performance liquid chromatography to produce a product; and
  (f) subjecting the product from step (e) to reverse phase high performance liquid chromatography to product purified differentiation inducing factor.

Bone marrow, either fetal or adult, human, or from other animals may also be used as a source of stem cells for purification of the differentiation inducing composition. For example, human fetal bones may be dissected from 21- to 24-week-old fetuses obtained by elective abortion with approved consent (i.e., from Anatomic Gift Foundation, White Oak, Ga.). To purify human HSCs, BM cell suspensions are prepared by flushing split long bones with RPMI 1640 containing 2% heat-inactivated FCS (Gemini Bio-Products, Inc, Calabasas, Calif.). Low-density (<1.077 g/mL) mononuclear cells are isolated (Lymphoprep; Nycomed Pharma, Oslo, Norway) and washed twice in staining buffer (SB) consisting of Hanks' balanced salt solution (HBSS) with 2% heat-inactivated FCS and 10 mmol/L HEPES. Samples are then incubated for 10 minutes with 1 mg/mL heat-inactivated human gammaglobulin (Gamimune; Miles Inc, Elkhart, Ind.) to block Fc receptor binding of mouse antibodies. Fluorescein isothiocyanate (FITC)-labeled CD34 monoclonal antibodies (MoAbs) and phycoerythrin (PE)-labeled thy-1 MoAbs are then added at 0.5 to 1 $\mu g/10^6$ cells in 0.1 to 0.3 mL SB for 20 minutes on ice. Control samples are incubated in a cocktail of FITC-labeled and PE-labeled isotype-matched MoAbs. Cells are washed twice in SB, resuspended in SB containing 1 $\mu g/mL$ propidium iodide (Molecular Probes Inc, Eugene, Oreg.), and sorted using the tri-laser fluorescence-activated cell sorter (FACS) MoFlo (Cytomation, Inc, Fort Collins, Colo.). Live cells (ie, those excluding propidium iodide) are always greater than 95%. Sort gates are set based on the mean fluorescence intensity of the isotype control sample. Cells are collected in 12- or 24-well plates in RPMI 1640 containing 10% FCS and 10 mmol/L HEPES, counted, and reanalyzed for purity in every experiment. Typically, 450,000 to 500,000 $CD34^+$ $thy-1^+$ cells are obtained from a single donor. MoAbs for CD34 are purchased from Becton Dickinson (Mountain View, Calif.). MoAbs for thy-1 and isotype controls are purchased from Pharmingen (San Diego, Calif.).

Using both the placental source described above or the bone marrow source of differentiation-inducing activity, concentration of this activity can be performed using solid phase extraction. $C_{18}$ cartridges (Mini-Spe-ed C18-14%, S.P.E. Limited, Concord ON) are prepared by washing with 10 ml of methanol followed by 10 ml 18 megaohm/cm deionized-distilled water. Up to 100 ml of supernatants of cultured cord blood stem cells are passed through each cartridge before elution. After washing the cartridges with 5 ml of deionized-distilled water, material adsorbed to the $C_{18}$ cartridge is eluted with 3 ml methanol, evaporated under a stream of nitrogen, redissolved in a small volume of methanol, and stored at 4° C. Before testing the eluate for differentiation inducing activity in vitro, the methanol is evaporated under nitrogen and replaced by culture medium.

$C_{18}$ cartridges can be used to adsorb small hydrophobic molecules from the cord blood stem cell culture supernatant, allowing the elimination of salts and other polar contaminants.

EXAMPLES

The following examples are offered to illustrate, but not to limit, the claimed invention.

1. CD34+ Cell Purification

Cord blood was obtained from consenting mothers undergoing cesarean delivery of healthy, full-term infants, and low-density (less than 1.077 g/ml) cells were isolated by centrifugation on Ficoll-Hypaque. $CD34^+$ cell-enriched populations (65-98% $CD34^+$ cells) were obtained by removal of lineage marker-positive cells using a column (n=2); and positive (EasySep) selection using magnetic beads (n=1; StemCell Technologies Inc.). Cells were stimulated overnight for in vivo experiments and for 48 hours for in vitro experiments at densities less than or equal to $2\times10^5$ cells/ml in Iscove's medium supplemented with 1% BSA, 10 $\mu g/ml$ bovine pancreatic insulin, and 200 $\mu g/ml$ human transferrin (BIT; StemCell Technologies Inc.), $10^{-4}$ mol 2-mercaptoethanol, 2 mM glutamine, 100 ng/ml FL (Immunex Corp.), 100 ng/ml SF, 50 ng/ml Tpo (Genentech Inc.), and 100 ng/ml hIL-6 (provided by S. Rose-John, Christian-Albrechts University, Kiel, Germany). The following day, the cells were pelleted, resuspended in fresh growth factor-supplemented medium with 5 $\mu g/ml$ protamine sulfate and $0.5\times10^8$ to $5\times10^8$ infectious units/ml (MOI=9-140; 140 in experiment 1, 9 and 90 in experiment 2), placed in a 24-well plate coated with 2 $\mu g/cm^2$ Retronectin (Takara Shuzo Co.) or with 5 $\mu g/cm^2$ fibronectin (Sigma-Aldrich), and then incubated at 37° C. for 6 hours.

2. Generation of Placental Lysate

Term placentas were harvested and the chorion was mechanically separated under sterile conditions. Placentas were collected in ice-cold Dutch modification of RPMI 1640 (Sigma, St. Louis, Mo.) supplemented with 10% FCS, 2 mM L-glutamine, gentamicin (25 $\mu g/ml$), and penicillin/streptomycin (100 U/ml) (complete medium). They were incubated with occasional agitation for 20 min at room temperature in calcium- and magnesium-free HBSS (Life Technologies, Paisley, U.K.) containing 1 mM DTT (Sigma). Purified cell homogenate was prepared by collagenase digestion. Briefly, bacterial collagenase (Advance Biofactures, Lynbrook, N.Y.) digestion was sequentially performed, 4 $\mu l$ of 50 mM calcium acetate was added, followed by 3 $\mu l$ (3 units) of bacterial collagenase. Reactions were then incubated for another 60 min at 37° C. Heparitinase digestions (15 $\mu l$) were carried out for 90 min at 37° C. in a pH 7.0 buffer consisting of 100 mM sodium acetate, 10 mM calcium acetate, using 5 milliunits of enzyme. In those reactions where bacterial collagenase digestion was sequentially performed, 4 µl of 5× collagenase buffer (250 mM Tris-HCl, pH 7.2, 50 mM calcium acetate) was added, followed by 3 µl (3 units) of bacterial collagenase. Reactions were then incubated for another 60 min at 37° C. Purified cells were subsequently sonicated, centrifuged at 10,000 g for 3 hours, and supernatant was collected, filter sterilized, and quantified for protein content using the Bradfort Assay.

3. Induction of HL-60 Differentiation In Vitro Using Cord Blood Co-Culture

As demonstrated in FIG. 1, coculture of 100,000 HL-60 human myelomonocytic leukemia cells with increasing numbers of cord blood nucleated cells resulted in an increased proportion of HL-60 cells differentiating into adherent monocytic cells. HL-60 cells were plated in 96 well plates at a concentration of 100,000 cells per well. The addition of cord blood nucleated cells was performed at the concentration indicated in the figure. The percentage of adherent cells was determined by a blinded observer. The fact that the HL-60 were truly differentiating was attested to by morphological changes (data not shown).

Figure 2:
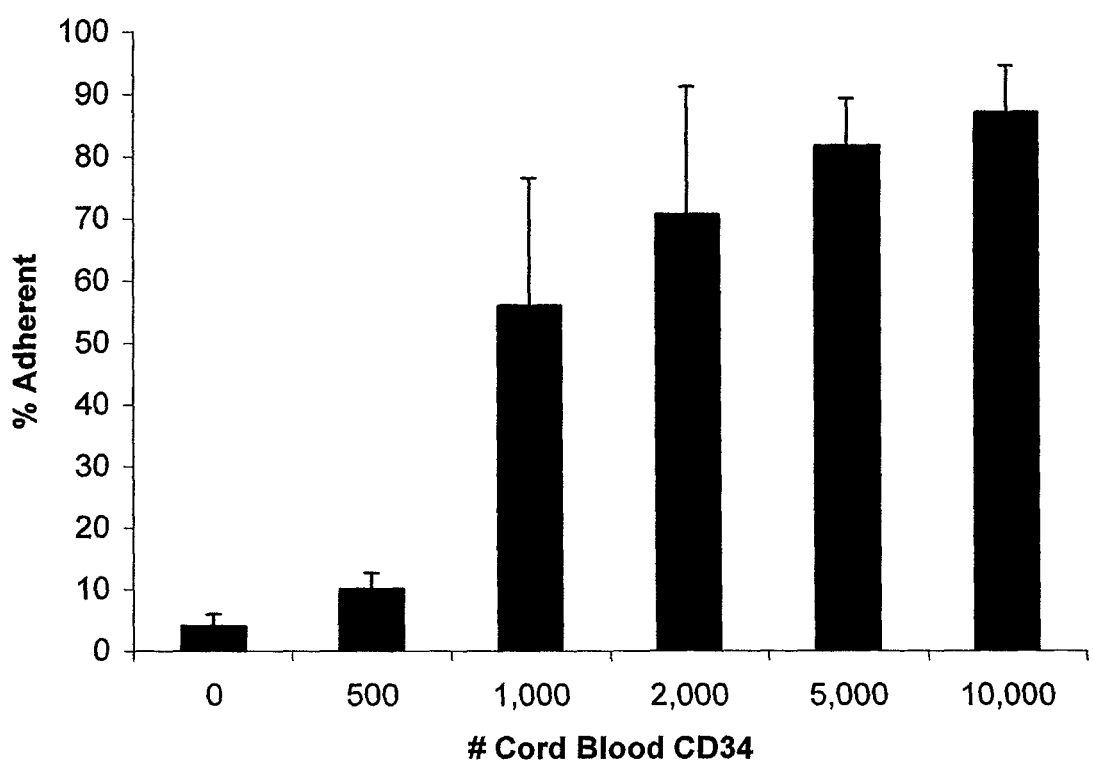
FIG. 2 is a bar graph demonstrating the induction of HL-60 differentiation in vitro by co-culture with cord blood CD34+ stem cells.

4. Induction of HL-60 Differentiation In Vitro Using Purified Cord Blood CD34+Cells As demonstrated in FIG. 2, coculture of 100,000 HL-60 human myelomonocytic leukemia cells with increasing numbers of CD34+ purified cord blood nucleated cells resulted in an increased proportion of HL-60 cells differentiating into adherent monocytic cells. HL-60 cells were plated in 96 well plates at a concentration of 100,000 cells per well. The addition of cord blood CD34+ cells was performed at the concentration indicated in the figure. The percentage of adherent cells was determined by a blinded observer. The fact that the HL-60 were truly differentiating was attested to by morphological changes (data not shown).

5. Induction of HL-60 Differentiation by Culture with Cord Blood Extracts

Figure 3:
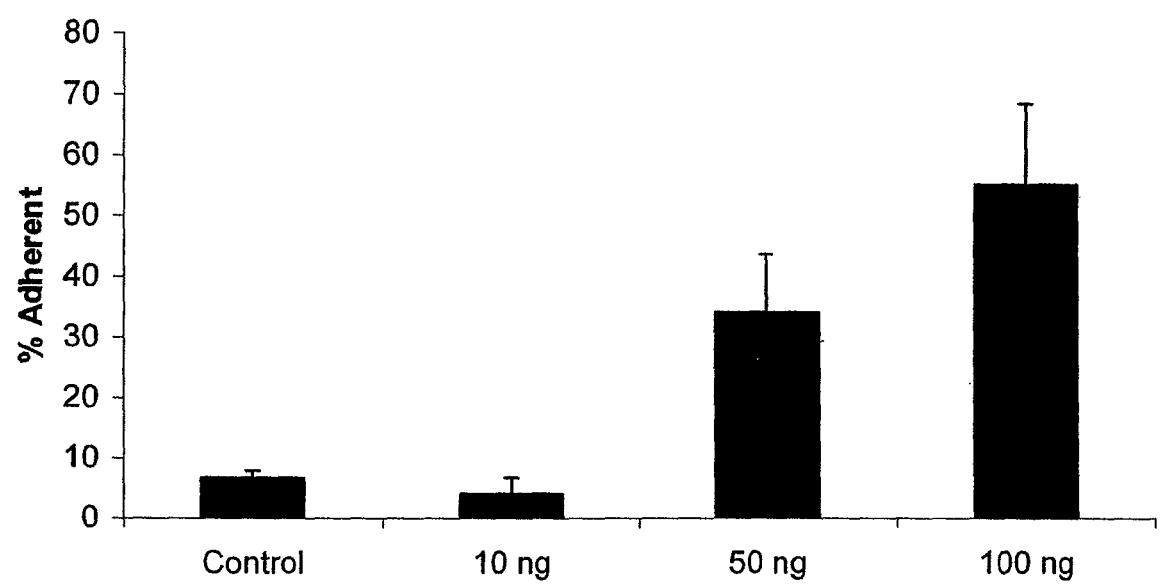
FIG. 3 is a bar graph demonstrating the induction of HL-60 differentiation by culture with placental extracts.

Cord blood extracts were prepared by culturing nucleated cells in Hanks media for 48 hours and the supernatant was concentrated using Solid Phase Extraction. $C_{18}$ cartridges (Mini-Spe-ed C18-14%, S.P.E. Limited, Concord ON) were prepared by washing with 10 ml of methanol followed by 10 ml 18 megaohm-cm deionized-distilled water. Up to 100 ml of supernatants of cultured cord blood stem cells are passed through each cartridge before elution. After washing the cartridges with 5 ml of deionized-distilled water, material adsorbed to the $C_{18}$ cartridge is eluted with 3 ml methanol, evaporated under a stream of nitrogen, redissolved in a small volume of methanol, and stored at 4° C. Before testing the eluate for differentiation inducing activity in vitro, the methanol is evaporated under nitrogen and replaced by culture medium. Before addition to the media, however, the concentration of $C_{18}$ extract was quantified using the Bradfort assay. The indicated concentration of cord blood extract was added to 100,000 proliferating HL-60 cells per well. As shown in FIG. 3, and increased number of differentiated HL-60 cells was observed after 48 hours.

6. Induction of HL-60 Differentiation by Placental Extracts

Figure 4:
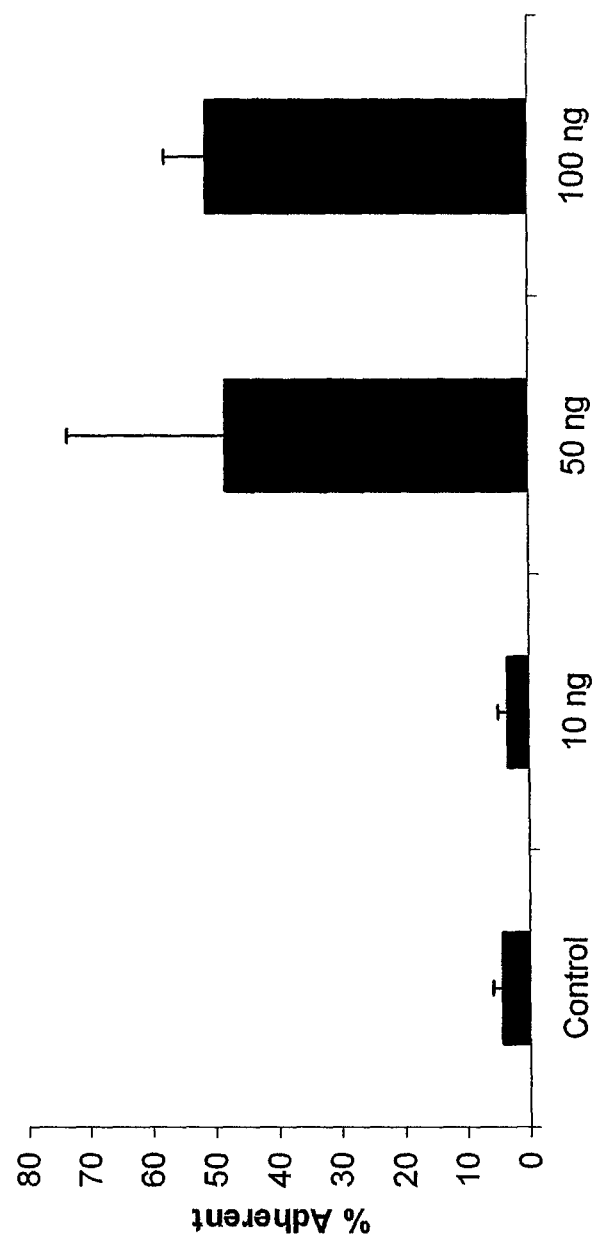
FIG. 4 is a bar graph demonstrating the induction of HL60 differentiation using cord blood extracts.
Figure 5:
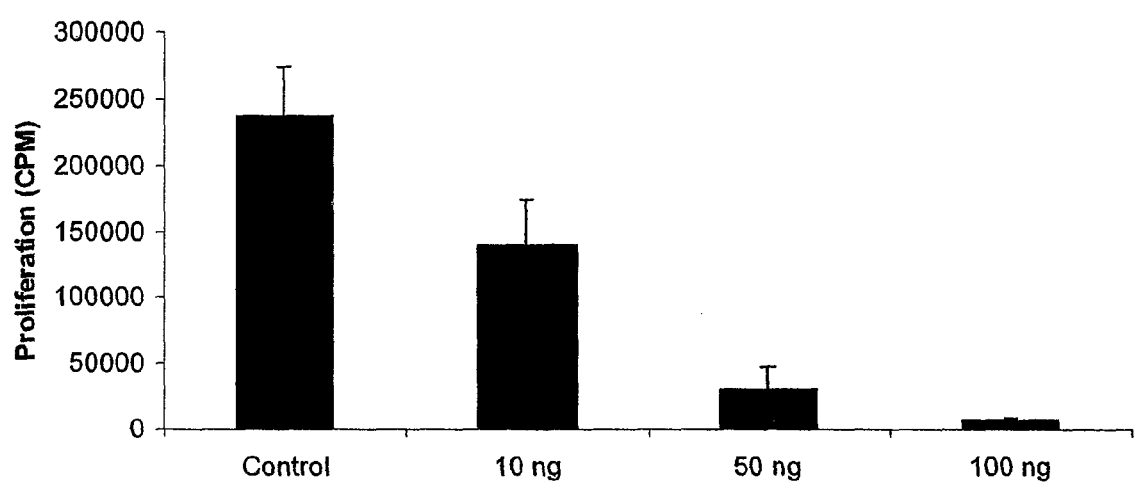
FIG. 5 is a bar graph demonstrating the inhibition of HL-60 proliferation by culture with placental extracts.
Figure 6:
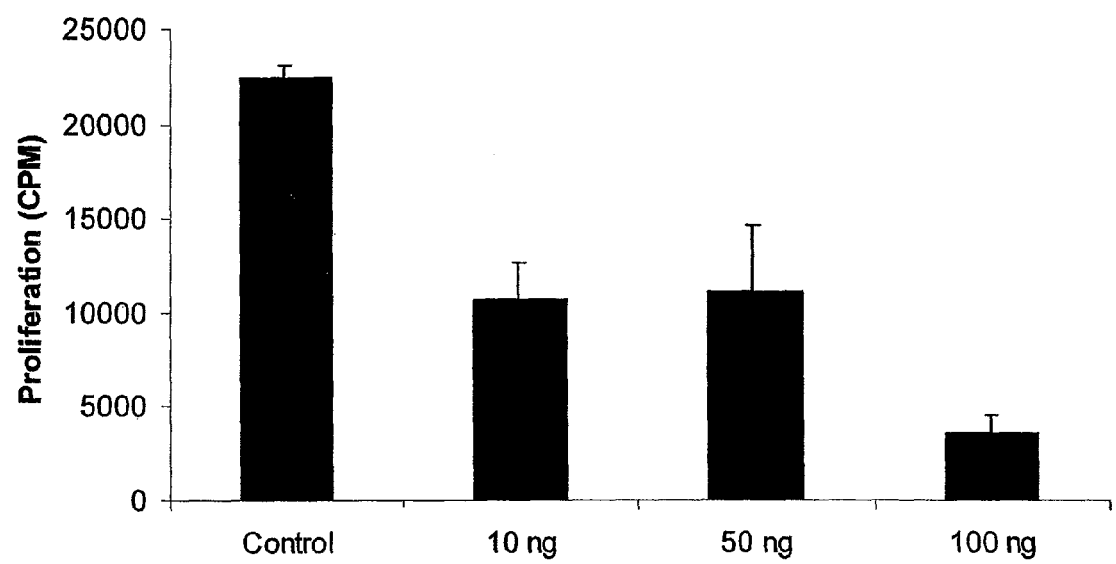
FIG. 6 is a bar graph demonstrating the inhibition of LNCaP proliferation by culture with placental extracts.
Figure 7:
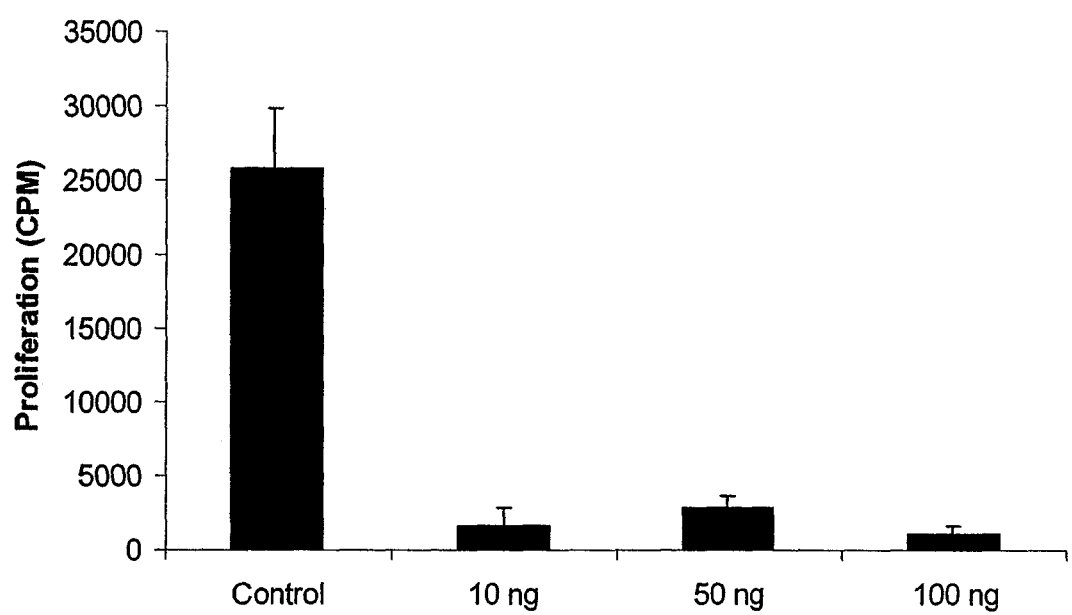
FIG. 7 is a bar graph demonstrating the inhibition of PC-3 proliferation by culture with placental extracts.
Figure 8:
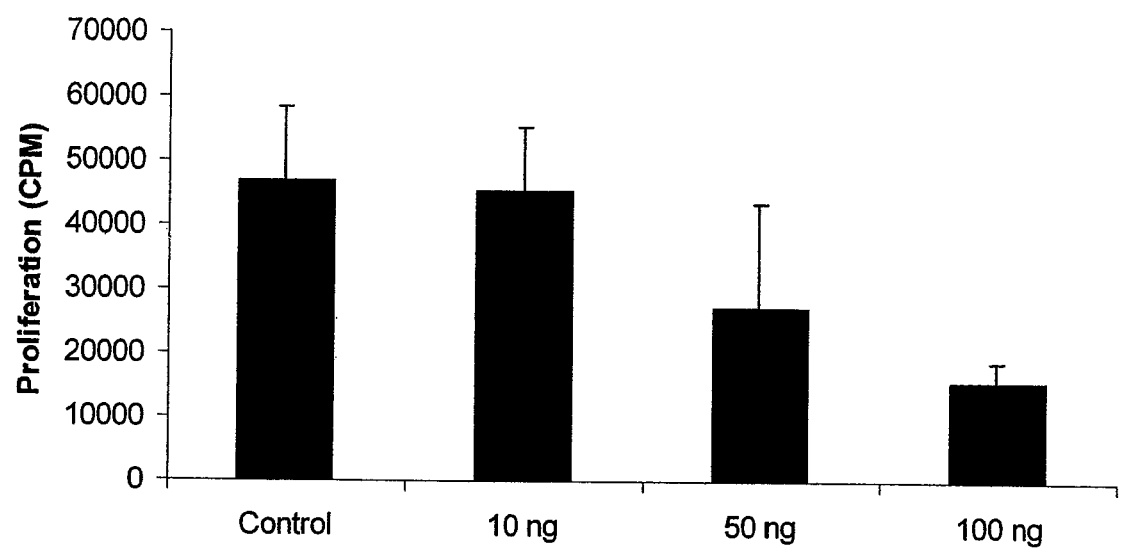
FIG. 8 is a bar graph demonstrating the inhibition of Lewis Lung Carcinoma cell proliferation by culture with placental extracts.

Placental extracts were derived and quantified as described above. The indicated concentration of cord blood extract was added to 100,000 proliferating HL-60 cells per well. As shown in FIG. 4, an increased number of differentiated HL-60 cells was observed after 48 hours. The extent of differentiation was dependent on the concentration of placental extract added.

7. Inhibition of Cancer Cell Proliferation by Culture with Placental Extracts HL-60, LNCaP, PC-3 and Lewis Lung carcinoma cells ($1 \times 10^5$/well) were plated in 96 well plates in 200 µl of RPMI 1640 (Life Technologies) supplemented with 10% FCS (Life Technologies), 100 U/ml of penicillin (Life Technologies), and 100 µg/ml of streptomycin (Life Technologies). Cells were cultured at 37° C. in a humidified atmosphere of 5% $CO_2$ for 3 days in the presence of the indicated about of placental extract, and pulsed with 1 µCi of [$^3$H]thymidine (Amersham Pharmacia Biotech) for the last 16 h of culture. Cells were harvested onto glass fiber filters, and the radioactivity incorporated was quantitated using a Wallac Betaplate liquid scintillation counter. Results were expressed as the mean cpm of triplicate cultures±SEM. As seen in FIGS. 5-8, a dose-dependent inhibition of tumor cell proliferation was noted in all 3 in vitro experimental tumor systems.

8. Inhibition of Cancer Cell Metastasis by Placental Extract

Lewis lung carcinoma (ATCC) were propagated by sequential subcutaneous transplantation in C57BL/6 mice. A single-cell suspension of tumor cells was prepared by mincing the tumor, followed by passage of the suspension first through a stainless steel mesh and then through a series of hypodermic needles of increasing gauge. This suspension of cells was aliquoted and frozen. For each series of injections, an aliquot of frozen tumor cells was thawed and expanded by culturing for 3 passages in Dulbecco's modified Eagle's medium (DMEM) containing 10% fetal calf serum, penicillin, and streptomycin. Before injection, the tumor cells were detached by trypsinization, washed once in cold DMEM containing 10% fetal calf serum, and once in cold serum-free medium. Cell viability was usually greater than 85%, as determined by trypan blue exclusion. The dorsal skin of mice was shaved 1 day before injection. The mice were anesthetized by Metofane inhalation, and tumor cells (500, 000) trypan blue-excluding cells in 100 µL) were injected into the dorsal subcutis using a 27-gauge needle.

Three weeks after tumor inoculation quantitation of lung metastasis was performed. Mice were killed using CO2 narcosis, and the lungs were removed, rinsed in phosphate-buffered saline (PBS), and placed in Bouin's fixative for at least 24 hours. The fixed lungs were carefully separated into individual lobes with forceps, and the number of surface metastases (appearing as white foci against a yellow background) was counted for each lobe using a dissecting microscope at 4× magnification (total metastatic foci) or by the naked eye (large metastatic foci).

Figure 9:
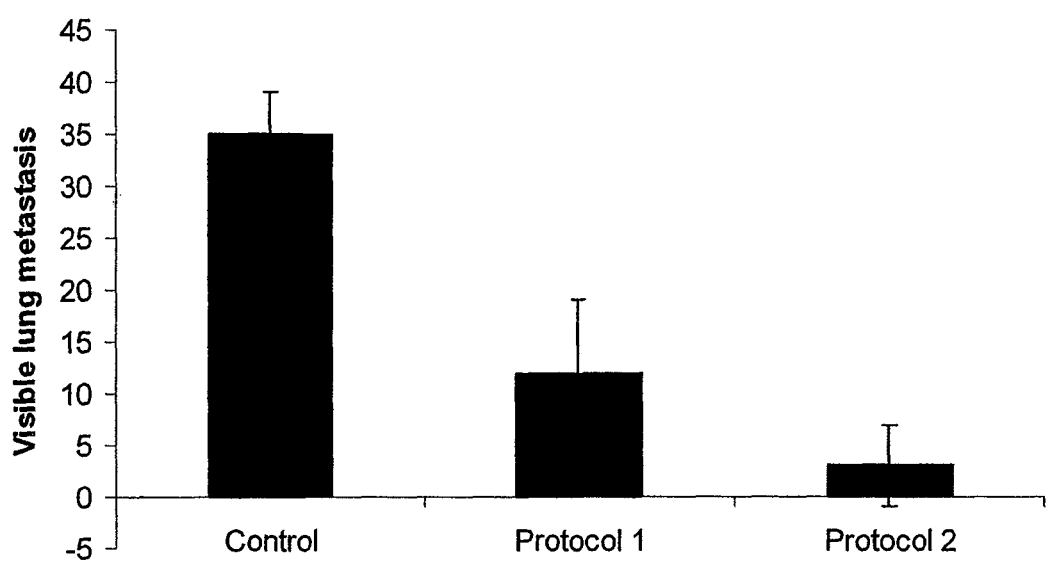
FIG. 9 is a bar graph demonstrating the inhibition of lung metastasis using placental extract in the Lewis Lung Carcinoma murine model of lung cancer.

Two treatment protocols were used. In the first one, 1 ug of placental extract was administered 1 day prior to tumor cell inoculation, in the second protocol 1 ug of placental extract was administered on days −1, 1, 4, and 7 in reference to tumor cell inoculation. As seen in FIG. 9, protocol 2 was most effective at decreasing the amount of visible tumor foci.

9. Inhibition of Tumor Growth by Placental Extract

C57/BL6 mice were inoculated with Lewis Lung Carcinoma cells as described in the above section. Tumor growth was quantitated by a blinded observer using calipers. The size of the tumor is represented in FIG. 10. As observed, the mice treated with Protocol 2 (described above) resulted in a significant inhibition of tumor growth. Although not illustrated, the survivors had a dense, fibrous scar-like tissue where the tumor used to be.

It will be apparent to one skilled in the art that varying substitutions and modifications can be made to the invention disclosed herein without departing from the scope and spirit of the invention.

Those skilled in the art recognize that the aspects and embodiments set forth herein can may be practiced separate from each other or in conjunction with each other. Therefore, combinations of separate embodiments are within the scope as disclosed herein.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions indicates the exclusion of equivalents of the features shown and described or portions thereof. It is recognized that various modifications are possible within the scope of the invention disclosed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the disclosure.

The following references are incorporated herein by reference in their entireties.

REFERENCES

1. Attar, E. C. and D. T. Scadden, *Regulation of hematopoietic stem cell growth*. Leukemia, 2004. 18(11): p. 1760-8.
2. Ema, H. and H. Nakauchi, *Self-renewal and lineage restriction of hematopoietic stem cells*. Curr Opin Genet Dev, 2003. 13(5): p. 508-12.
3. Craig, C. E., et al., *The histopathology of regeneration in massive hepatic necrosis*. Semin Liver Dis, 2004. 24(1): p. 49-64.
4. Kaur, P., et al., *Keratinocyte stem cell assays: an evolving science*. J Investig Dermatol Symp Proc, 2004. 9(3): p. 238-47.
5. Rookmaaker, M. B., et al., *Progenitor cells in the kidney: biology and therapeutic perspectives*. Kidney Int, 2004. 66(2): p. 518-22.
6. Chaudhari, M., et al., *Pancreatic stem cells: a therapeutic agent that may offer the best approach for curing type 1 diabetes*. Pediatr Diabetes, 2001. 2(4): p. 195-202.
7. Brittan, M. and N. A. Wright, Gastrointestinal stem cells. J Pathol, 2002. 197(4): p. 492-509.
8. Martino, G., How the brain repairs itself: new therapeutic strategies in inflammatory and degenerative CNS disorders Lancet Neurol, 2004. 3(6): p. 372-8.
9. Liu, L., et al., Epigenetic regulation of human telomerase reverse transcriptase promoter activity during cellular differentiation. Genes Chromosomes Cancer, 2004. 41(1): p. 26-37.
10. Lodygin, D., J. Diebold, and H. Hermeking, Prostate cancer is characterized by epigenetic silencing of 14-3-3sigma expression. Oncogene, 2004. 23(56):9034-9041.
11. Mhawech, P., et al., Downregulation of 14-3-3sigma in ovary, prostate and endometrial carcinomas is associated with CpG island methylation. Mod Pathol, 2004. 18(3): 340-348.
12. de Vries, E. G., et al., The happy destiny of frozen haematopoietic stem cells: from immature stem cells to mature applications. Eur J Cancer, 2004. 40(13): p. 1987-92.
13. Rocha, V., G. Sanz, and E. Gluckman, Umbilical cord blood transplantation. Curr Opin Hematol, 2004. 11(6): p. 375-385.
14. Michel, G., et al., Unrelated cord blood transplantation for childhood acute myeloid leukemia: a Eurocord Group analysis. Blood, 2003. 102(13): p. 4290-7.
15. Hall, J. G., et al., *Unrelated umbilical cord blood transplantation for an infant with beta-thalassemia major*. J Pediatr Hematol Oncol, 2004. 26(6): p. 382-5.

What is claimed is:

1. A method of inhibiting growth of a neoplastic cell, the method comprising:
   (a) providing a cell free-placental extract made by the process comprising:
      (i) obtaining human placenta;
      (ii) homogenizing the obtained human placenta by digesting the obtained human placenta with a collagenase and a heparitinase, wherein the heparitinase digestion is at a neutral pH, the homogenization resulting in a homogenate;
      (iii) centrifuging said homogenate to produce a supernatant free of cellular debris; and
      (iv) purifying the supernatant to obtain cell free-placental extract comprising a cell differentiation-inducing fraction having a molecular weight in the range from about 10 Daltons to about 10,000 Daltons
   (b) directly administering said cell free-placental extract to the neoplastic cell which is selected from the group consisting of a leukemia cell, and a prostate cancer cell, thereby inhibiting growth of the neoplastic cell.

2. The method of claim 1, wherein the step (iv) of purifying comprises running the supernatant through adsorption on a C-18 column, and then filter sterilizing the purified supernatant.

3. The method of claim 1, wherein the neoplastic cell is in vivo.

4. The method of claim 1, wherein the neoplastic cell is in vitro.

5. The method of claim 1, wherein the administered cell free-placental extract is in a liposomal complex.

6. The method of claim 1, wherein a histone deacetylase inhibitor is added to the extract prior to the administration of said cell free placenta.

7. The method of claim 1, wherein the step(ii) further comprises sonicating the the homogenate.

* * * * *